(12) United States Patent
Rozga et al.

(10) Patent No.: US 6,207,448 B1
(45) Date of Patent: Mar. 27, 2001

(54) BIOREACTOR AND RELATED METHOD

(75) Inventors: Jacek Rozga, Westlake Village; Achilles A. Demetriou, Bel Air, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/145,586

(22) Filed: Sep. 2, 1998

(51) Int. Cl.$^7$ .............................. C12P 1/00; C12M 1/12; C02F 3/02
(52) U.S. Cl. .................. 435/297.4; 435/260; 435/286.5; 435/297.4; 210/620; 210/629; 210/321.8; 210/321.89
(58) Field of Search .............................. 435/286.1, 286.5, 435/293.1, 297.1, 297.2, 297.4, 818, 41, 393, 420, 260; 210/620, 629, 321.69, 321.79, 321.8, 321.88, 321.89

(56) References Cited

U.S. PATENT DOCUMENTS

| 3,997,396 | 12/1976 | Delente . |
| 4,647,539 | * 3/1987 | Bach . |
| 4,804,628 | 2/1989 | Cracauer et al. ............. 435/240.242 |
| 4,889,812 | 12/1989 | Guinn et al. ......................... 435/289 |
| 5,110,741 | 5/1992 | Ohi et al. . |

FOREIGN PATENT DOCUMENTS

| 0 343 394 A1 | 11/1988 | (EP) . |
| WO 8602379 | 4/1986 | (WO) . |

OTHER PUBLICATIONS

PCT Search Report dated Jan. 6, 2000.

* cited by examiner

*Primary Examiner*—David A. Redding
(74) *Attorney, Agent, or Firm*—Sidley & Austin

(57) ABSTRACT

A bioreactor (10) comprises an elastic housing (12) and a plurality of hollow, porous fibers (14) disposed within the housing. The lumens of the fibers define an intrafiber compartment, and the outer surfaces of the fibers and the housing define an extrafiber compartment. A variable flow device (34) varies the flow of the perfusate through the intrafiber compartment. The variable flow device can include a flow restrictor (34) that variably restricts the discharge of a perfusate (26) from the intrafiber compartment or a pump for increasing the flow of the perfusate into the intrafiber compartment. The elastic housing can include a wall (28) with perforations (30) extending therethrough and an elastic membrane (32) tightly surrounding the wall or a wall with at least one expansion port extending therethrough and at least one extrafiber space expander 38 coupled to a one of the at least one expansion port.

23 Claims, 2 Drawing Sheets

BIOREACTOR AND RELATED METHOD

FIELD OF THE INVENTION

The present invention relates generally to the field of biomedicine, and more particularly, to cell culture devices and artificial organs and methods therefore. Although the invention is subject to a wide range of applications, it is especially suited for use in a bioreactor, and will be particularly described in that connection.

BACKGROUND OF THE INVENTION

Various bioreactors used as cell culture devices and artificial organs are known. Typically, the known bioreactors utilize hollow-fiber technology. An array of hollow-fiber reactors exists as filters, membrane oxygenators, plasma separators, and cell line producers.

Commonly, a bundle of small-diameter hollow, porous fibers are contained in a housing that is rigid and sealed. The bundle of fibers is stretched so that the individual fibers run in parallel to each other. The ends of the bundle are sealed at each end so that two compartments are formed: intrafiber that is within the lumens of the fibers and extrafiber that is outside the fibers but still within the housing.

A biological component is loaded into the extrafiber compartment, and a perfusate is typically pumped through the intrafiber compartment. A mass transfer from the intrafiber compartment across the fiber wall into the extrafiber compartment is dependent primarily on convection. During convection, also known as Starling flow, only a small fraction of the perfusate moves to the extrafiber compartment and then returns back to the intrafiber compartment. The driving force behind this phenomenon is a pressure gradient that develops during perfusion along a long axis of the bioreactor. In the known hollow-fiber bioreactors, convection can be increased through the increase in the rate of axial flow.

However, when the conventional hollow-fiber bioreactor is seeded with a biological component, such as, cells, and used as an extracorporeal artificial organ, the rate of axial flow cannot be increased significantly without causing damage to blood cells (hemolysis) and biological component due to excessive sheering pressure.

A need therefore exists for a bioreactor, and a method therefore, that increases the mass transport across the fiber wall under low flow and low pressure conditions.

SUMMARY OF THE INVENTION

The present invention, which tends to addresses this need, resides in a bioreactor. The bioreactor described herein provides advantages over known bioreactors in that it provides increased mass transport across the fiber wall.

According to the present invention, the foregoing advantage is principally provided by forcing a perfusate from an intrafiber compartment into an extrafiber compartment and then forcing the perfusate in the extrafiber compartment back into the intrafiber compartment. This can be accomplished by the use of an elastic housing and a variable flow device for varying the flow of a perfusate through the intrafiber compartment. Thus, a bi-directional mass transport across the fiber wall is increased.

In accordance with one aspect of the invention, variably restricting the discharge of the perfusate from the intrafiber compartment. This can be accomplished by use of a flow restrictor. The variation in discharge results in peaks and valleys (pulsations) in the intrafiber pressure. During restriction of the discharge, the perfusate passes through the pores of the fibers because of the increase in flow resistance, the volume of perfusate in the extrafiber compartment increases causing the perfusate in the extrafiber compartment to distend the elastic housing. During loosening of the restriction of discharge, the elastic housing contracts to reverse the flow of the perfusate through the pores and force it back into the intrafiber compartment.

In accordance with one aspect of the invention, variably increasing the flow of the discharge of the perfusate through the intrafiber compartment. This can be accomplished by use of a pump. During increase in flow of the discharge, the perfusate passes through the pores of the fibers because of the increase in flow resistance, the volume of perfusate in the extrafiber compartment increases causing the perfusate in the extrafiber compartment to distend the elastic housing. During decrease in flow of the perfusate, the elastic housing contracts to reverse the flow of the perfusate through the pores and force it back into the intrafiber compartment.

In accordance with still another aspect of the invention, varying the flow of the perfusate according to a pressure of the extrafiber compartment. This can be accomplished by a pressure monitor that measures the pressure in the extrafiber compartment and the variable flow device being responsive to the measured pressure. Thus, the amount of bi-directional mass transport across the fiber walls can be controlled by the amplitude of pulsations in perfusion pressure.

In accordance with another aspect of the invention, the elastic housing includes a wall with perforations extending therethrough and an elastic material tightly surrounding the wall. During restriction of the discharge, the membrane distends. During loosening of the restriction of discharge, the membrane contracts.

In accordance with still another aspect of the invention, the elastic housing includes a wall with at least one expansion port extending therethrough and at least one extrafiber space expander coupled to a one of the at least one expansion port. During restriction of the discharge, the at least one expansion port distends. During loosening of the restriction of discharge, the at least one expansion port expands.

In accordance with the method of this invention, providing an elastic housing and varying the flow of the perfusate through the intrafiber compartment.

The method more particularly comprises measuring a pressure in the extrafiber compartment and varying the flow of the perfusate through the intrafiber compartment in response to the measured pressure.

Other features and advantages of the present invention will be set forth in part in the description which follows and accompanying drawings, wherein the preferred embodiments of the invention are described and shown, and in part become apparent to those skilled in the art upon examination of the following detailed description taken in conjunction with the accompanying drawings, or may be learned by practice of the invention. The advantages of the invention may be realized and attained by means of the instrumentalities and combinations particularly pointed out in the appended claims.

DESCRIPTION OF THE PREFERRED EMBODIMENTS

Figure 1:
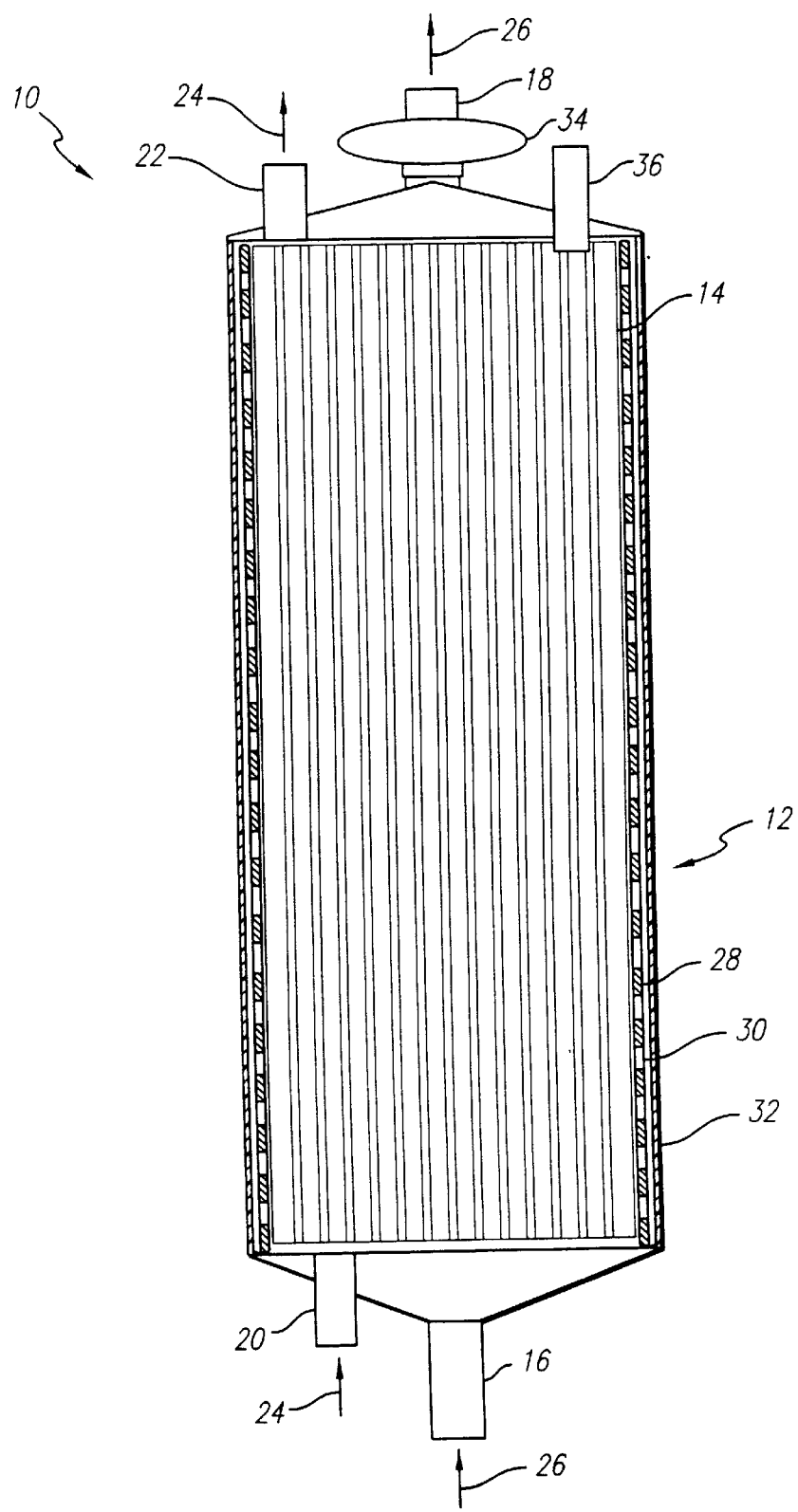
FIG. 1 is a partial-section elevational view of a bioreactor with the internals of the housing shown in section.

As shown in the exemplary drawing, the present invention is embodied in a bioreactor 10 comprising a housing 12, a plurality of fibers 14, an inflow port 16, an outflow port 18, an inlet port 20, and an outlet port 22.

The plurality of hollow, porous fibers 14 are stretched so that the individual fibers 14 run in parallel to each other. The ends of the bundle are sealed at each end so that two compartments are formed: intrafiber that is within the lumens of the fibers 14 and extrafiber that is outside the fibers 14 but still within the housing 12.

The inlet port 20, which is coupled with the extrafiber compartment, is used to seed or replace a biological component 24 in the extrafiber compartment. The outlet port 22, which is also coupled with the extrafiber compartment, is used to remove the spent biological component 24 from the extrafiber compartment.

A perfusate 26 is pumped through the intrafiber compartment via the inflow port 16, which is communicatively coupled with the intrafiber compartment and admits the perfusate 26 to flow into the intrafiber compartment. The perfusate 26 migrates to the extrafiber compartment via the pores in the fibers 14. The outflow port 18, which is coupled with the intrafiber compartment, discharges the perfusate 26 from the intrafiber compartment.

In one exemplary application as a bioreactor for perfusion cell culture, the extrafiber compartment is loaded with a biological component, such as, isolated cells, tissue, cell/tissue fragments, or microorganisms, for example, bacteria, fungi, or the like. The biological component is perfused, via the porous fibers, with a culture medium and products of interest. The products of interest are synthesized by the biological component and collected.

In another exemplary application as an extracorporeal artificial organ, the biological component is seeded into the extrafiber compartment, and the biological component is perfused, via the porous fibers, in vitro or in vivo with a patient's blood or plasma. In this way, blood or plasma can be purified from unwanted compounds or supplemented with factors synthesized by the biological component.

In accordance with one embodiment of the present invention, the housing 12 includes a substantially cylindrical wall 28 having an interior surface and exterior surface with perforations 30 extending therethrough, and an elastic membrane 32 tightly surrounding the exterior surface of wall 28. The plurality of fibers 14 are disposed in the wall 28. A variable flow device, such as, flow restrictor 34, is coupled to the outflow port 18 to variably restrict the discharge of the perfusate 26 from the intrafiber compartment as it is pumped through the intrafiber compartment. During restriction of the discharge, the perfusate 26 passes through the pores of the fibers because of the increase in flow resistance, the volume of perfusate 26 in the extrafiber compartment increases causing the perfusate 26 in the extrafiber compartment to be forced through the perforations 30, which in turn causes the housing 12, or, more particularly, the membrane 32, to distend. During loosening of the restriction of the discharge, the membrane 32 contracts to reverse the flow of the perfusate 26 through the pores and forces it back into the intrafiber compartment. Thus, an increased mass transport over conventional bioreactors that rely on convection occurs across the fiber wall. Accordingly, the bioreactor can be made more compact and axial flow can be decreased.

In the exemplary application as a bioreactor for perfusion cell culture, an increased bi-directional mass transport allows for much faster access of substrates to the biological component back to the perfusate flowing through the intrafiber compartment.

In the exemplary application as an extracorporeal artificial organ, an increased bi-directional mass transport allows for much faster access of substrates to the biological component in the extrafiber compartment, much higher rate of processing (metabolism) of such substrates by the biological component, and much faster delivery of products synthesized by the biological component back to the intrafiber compartment.

The wall 28 can be composed of a polycarbonate material or any other suitable rigid material. The perforations 30 can be about 5 micron or larger in diameter, depending upon the unit size of the biological component, to allow free flow of the perfusate 26 outside the wall 28, but, at the same time, to prevent the translocation of the biological component through the perforations 30 outside the wall 28.

The membrane 32 can be an elastic material composed of a latex or any other suitable material with elastic properties.

The plurality of fibers 14 can be composed of cellulose nitrate or polysulfone, or any other suitable porous material, and have pores less than 2 microns in diameter.

The variable flow device can also include a pressure monitor 36 in communication with the extrafiber compartment and which measures the pressure in the extrafiber compartment. The variable flow device is responsive to the measured pressure to vary the flow of the perfusate 26 through the intrafiber compartment. In one exemplary embodiment, the flow restrictor 34 intermittently restricts the discharge of the perfusate 26 at a rate of about 1 to 60 times per minute for about 1 to 30 seconds at a time.

Figure 2:
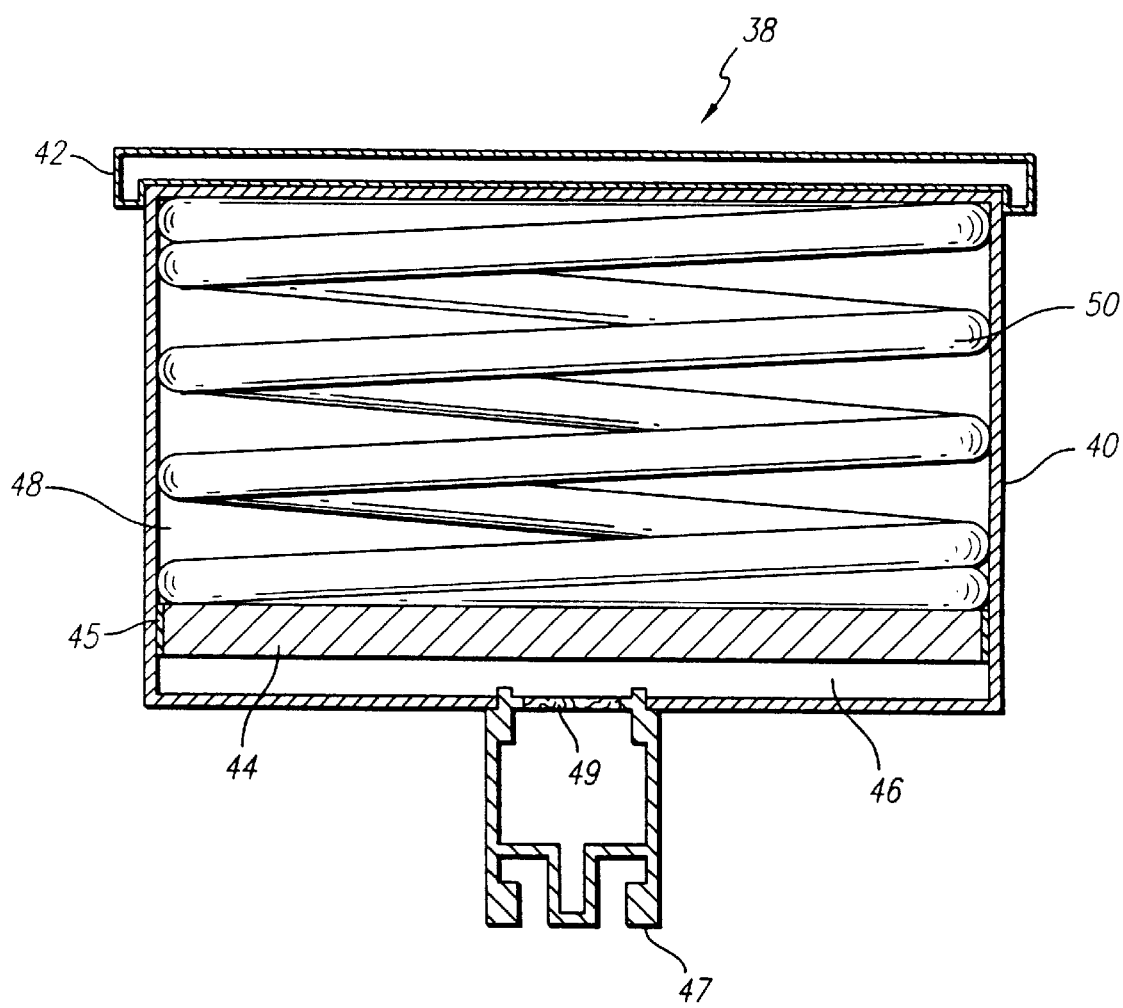
FIG. 2 is a cross-sectional view of an extrafiber space expander.

The invention is capable of other and different embodiments, and its several details are capable of modification, all without departing from the scope of the invention. For example, the variable flow device can include a pump, rather than the flow restrictor 34, coupled to the inflow port and which can variably increase the flow of the perfusate into the intrafiber compartment. Further, the housing can include an extrafiber space expander 38, as shown in FIG. 2, rather than the perforated wall 28 and elastic membrane 32. In this embodiment, the wall of the housing 12 is unperforated but has at least one expansion port extending therethrough. The at least one extrafiber space expander 38 is coupled to a one of the at least one expansion port and the extrafiber space expander 38 is in communication with the extrafiber space.

The at least one extrafiber space expander 38 includes a substantially cylindrical wall 40 closed at one end by a cap 42. Also, a piston 44 divides the chamber defined by the wall 40 and the cap 42 into two portions. A gasket 45 circumscribing the periphery of the piston 44 makes for a fluid-tight seal between the two portions.

One portion 46 of the chamber is in communication with the extrafiber compartment by way of the at least one expansion port. A standard Luer connector 47 can be used to couple the extrafiber space expander 38 to the expansion port. A microporous filter 49, disposed in or adjacent the opening leading to the connector 47, can keep unwanted material from entering the portion 46.

In the another portion 48 of the chamber, a spring 50 is disposed to bias the piston 44.

When the pump and the extrafiber space expander are used in combination, during increase in flow of the perfusate, the perfusate passes through the pores of the plurality of the fibers, the volume of perfusate in the extrafiber compartment increases causing the perfusate in the extrafiber compartment to flow through the at least one expansion port into the at least one extrafiber space expander. During decrease in flow of the perfusate, the perfusate in the extrafiber compartment is forced into the intrafiber compartment under the force of the at least one extrafiber space expander.

Those skilled in the art will recognize that various modifications and variations can be made in the bioreactor of the present invention and in construction and operation of this bioreactor without departing from the scope or spirit of this invention. For example, the pump and elastic membrane can be used in combination, the flow restrictor and extrafiber space expander can be used in combination, the pump can be coupled to the outlet port to variably restrict the discharge of the perfusate from the intrafiber compartment, multiple extrafiber space expanders can be used, and conventional bioreactors can be modified into pulsatile types by fitting them with a pulsatile pump and at least one extrafiber space expander

What is claimed is:

1. A bioreactor comprising:
    an elastic housing wherein the elastic housing includes,
        a wall with perforations extending therethrough, and
        an elastic membrane tightly surrounding the wall;
    a plurality of hollow, porous fibers disposed within the housing, the lumens of the fibers define an intrafiber compartment, and the exterior of the fibers and the housing define an extrafiber compartment; and
    a variable flow device for varying the flow of a perfusate through the intrafiber compartment.

2. The bioreactor of claim 1, wherein the variable flow device includes a flow restrictor for variably restricting the discharge of the perfusate from the intrafiber compartment.

3. The bioreactor of claim 2, wherein the flow restrictor variably restricts the flow of the perfusate for about 1 to 30 seconds.

4. The bioreactor of claim 2, wherein the flow restrictor variably restricts the discharge of the perfusate at a rate of about 1 to 60 times per minute.

5. The bioreactor of claim 1, wherein the variable flow device includes a pump for variably increasing the flow of the perfusate into the intrafiber compartment.

6. The bioreactor of claim 5, wherein the pump variably increases the flow of the perfusate for about 1 to 30 seconds.

7. The bioreactor of claim 5, wherein the pump variably increases the flow of the perfusate at a rate of about 1 to 60 times per minute.

8. The bioreactor of claim 1, wherein the variable flow device includes a pressure monitor for measuring a pressure in the extrafiber compartment, and the variable flow device varies the flow of the perfusate in response to the pressure.

9. The bioreactor of claim 1 further comprises:
    an inlet port, coupled with the extrafiber compartment, for seeding the extrafiber compartment with a biological component; and
    an outlet port, coupled with the extrafiber compartment, for removing the biological component from the extrafiber compartment.

10. The bioreactor of claim 1, wherein the wall is composed of a polycarbonate or other rigid material.

11. The bioreactor of claim 1, wherein the perforations are greater than about 5 microns in diameter.

12. The bioreactor of claim 1, wherein the elastic membrane is composed of a latex material.

13. The bioreactor of claim 1, wherein the plurality of hollow, porous fibers are composed of cellulose nitrate.

14. The bioreactor of claim 1, wherein the plurality of hollow, porous fibers are composed of polysulfone.

15. The bioreactor of claim 1, wherein the pores of the plurality of hollow, porous fibers are less than 2 microns in diameter.

16. A bioreactor comprising:
    a housing including,
        a wall substantially cylindrical in shape having an interior surface and an exterior surface and with perforations extending therethrough, and
        a membrane of elastic material tightly surrounding the exterior surface;
    a plurality of fibers disposed within the housing, each fiber substantially cylindrical in shape having an inner surface and an outer surface and with pores extending through the inner surface and outer surface, wherein the inner surface defines a lumen of each fiber, the lumens define an intrafiber compartment, and the outer surfaces and the housing define an extrafiber compartment;
    an inflow port, coupled with the intrafiber compartment, for admitting a perfusate to flow into the intrafiber compartment, wherein the perfusate migrates to the extrafiber compartment via the pores;
    an outflow port, coupled with the intrafiber compartment, for discharging the perfusate from the intrafiber compartment; and
    a flow restrictor, coupled to the outflow port, for variably restricting the discharge of the perfusate from the intrafiber compartment; wherein,
        during restriction of the discharge, the perfusate passes through the pores of the plurality of fibers, the volume of perfusate in the extrafiber compartment increases causing the perfusate in the extrafiber compartment to distend the membrane, and
        during loosening of the restriction of the discharge, the membrane contracts to reverse the flow of the perfusate through the pores.

17. A bioreactor comprising:
    a housing including,
        a wall substantially cylindrical in shape having an interior surface and an exterior surface and with perforations extending therethrough, and
        a membrane of elastic material tightly surrounding the exterior surface;
    a plurality of fibers disposed within the housing, each fiber substantially cylindrical in shape having an inner surface and an outer surface and with pores extending through the inner surface and outer surface, wherein the inner surface defines a lumen of each fiber, the lumens define an intrafiber compartment, and the outer surfaces and the housing define an extrafiber compartment;
    an inflow port, coupled with the intrafiber compartment, for admitting a perfusate to flow into the intrafiber compartment, wherein the perfusate migrates to the extrafiber compartment via the pores;
    an outflow port, coupled with the intrafiber compartment, for discharging the perfusate from the intrafiber compartment; and
    a pump, coupled to the inflow port, for variably increasing the flow of the perfusate into the intrafiber compartment; wherein,
        during increase in flow of the perfusate, the perfusate passes through the pores in the plurality of fibers, the volume of perfusate in the extrafiber compartment increases causing the perfusate in the extrafiber compartment to distend the membrane, and
        during decrease in flow of the perfusate, the membrane contracts to reverse the flow of the perfusate through the pores.

18. A method of perfusion in a bioreactor including a housing and a plurality of hollow, porous fibers disposed within the housing, the lumens of the fibers define an intrafiber compartment, and the exterior of the fibers and the housing define an extrafiber compartment, the method comprising:

providing an elastic housing including providing a wall with perforations extending therethrough and an elastic membrane tightly surrounding the wall; and varying the flow of a perfusate through the intrafiber compartment.

19. A method of perfusion in a bioreactor including a housing having a wall substantially cylindrical in shape with an interior surface and an exterior surface and a plurality of hollow, porous fibers disposed within the housing, the lumens of the fibers define an intrafiber compartment, and the exterior of the fibers and the housing define an extrafiber compartment, the method comprising:

providing perforations extending through the interior surface and the exterior surface of the wall;

tightly surrounding the exterior surface with a membrane of elastic material; and variably restricting the discharge of a perfusate from the intrafiber compartment.

20. A method of perfusion in a bioreactor including a housing having a wall substantially cylindrical in shape with an interior surface and an exterior surface and a plurality of hollow, porous fibers disposed within the housing, the lumens of the fibers define an intrafiber compartment, and the exterior of the fibers and the housing define an extrafiber compartment, the method comprising:

providing perforations extending through the interior surface and the exterior surface of the wall;

tightly surrounding the exterior surface with a membrane of elastic material; and variably increasing the flow of a perfusate into the intrafiber compartment.

21. The method of claim 18, wherein varying the flow of the perfusate through the intrafiber compartment includes variably restricting the discharge of the perfusate from the intrafiber compartment.

22. The method of claim 18, wherein varying the flow of the perfusate through the intrafiber compartment includes variably increasing the flow of the perfusate into the intrafiber compartment.

23. The method of claim 18 further comprising:

measuring a pressure in the extrafiber compartment;

wherein the flow of the perfusate through the intrafiber compartment is varied in response to the measured pressure.

* * * * *